(12) United States Patent
Young (10) Patent No.: US 8,751,934 B2
(45) Date of Patent: Jun. 10, 2014

(54) METHOD FOR ADJUSTING PARAMETERS OF AUDIO DEVICE

(75) Inventor: Shuenn-Tsong Young, Hsinchu (TW)

(73) Assignee: Alpha Networks Inc., Hsinchu (TW)

( * ) Notice: Subject to any disclaimer, the term of this patent is extended or adjusted under 35 U.S.C. 154(b) by 470 days.

(21) Appl. No.: 12/494,785

(22) Filed: Jun. 30, 2009

(65) Prior Publication Data
US 2010/0235747 A1      Sep. 16, 2010

(30) Foreign Application Priority Data
Dec. 26, 2008   (TW) ................................ 97151075 A (51) Int. Cl.
*G06F 3/00* (2006.01)
*G06F 3/16* (2006.01)

(52) U.S. Cl.
USPC ......................................... 715/727; 715/716

(58) Field of Classification Search
USPC .................................................. 715/727, 716
See application file for complete search history.

(56) References Cited

U.S. PATENT DOCUMENTS

| | | | |
|---|---|---|---|
| 6,067,084 A * | 5/2000 | Fado et al. ..................... | 715/708 |
| 7,450,724 B1 | 11/2008 | Greminger | |
| 7,610,553 B1 * | 10/2009 | Jacklin et al. ................. | 715/727 |
| 2002/0108484 A1 | 8/2002 | Arnold et al. | |
| 2007/0009126 A1 * | 1/2007 | Fischer ......................... | 381/315 |
| 2008/0072896 A1 | 3/2008 | Setzer et al. | |
| 2009/0164905 A1 * | 6/2009 | Ko ................................ | 715/727 |

FOREIGN PATENT DOCUMENTS

| | | |
|---|---|---|
| AU | 2005222499 B2 | 5/2006 |
| CN | 1371589 | 9/2002 |
| CN | 1780499 | 5/2006 |

OTHER PUBLICATIONS

China Patent Office Action, Sep. 5, 2011.

* cited by examiner

*Primary Examiner* — Weilun Lo
*Assistant Examiner* — Truc Chuong
(74) *Attorney, Agent, or Firm* — WPAT, PC; Justin King (57) ABSTRACT

A method for adjusting parameters of an audio device is provided and applied to an adjusting system operated by a user to adjust the audio device. The method includes steps of: executing an application program with the adjusting system; the application program providing a graphical user interface for receiving data wherein the graphical user interface at least includes a plurality of options to be selected; and adjusting a plurality of parameters of the audio device associated with a first option when the first option of the plurality options is selected and outputting a sound by the audio device.

15 Claims, 6 Drawing Sheets

METHOD FOR ADJUSTING PARAMETERS OF AUDIO DEVICE

FIELD OF THE INVENTION

The present invention relates to a method for adjusting parameters of an audio device, and more particularly to a method for adjusting parameters of an audio device by using an adjusting system to perform the adjustment of the audio device.

BACKGROUND OF THE INVENTION

Hearing loss is a serious problem affecting one's communication ability. According to statistics, about one third of senior citizens in Taiwan encounter hearing problems. Hearing problems not only result in communication difficulty, but also affect the quality of life. At worst, people having hearing impairments are unaware of surrounding dangers. Hence, hearing problem is an important healthy subject. For example, most degenerative presbycusis results from the death of inner hair cells, vascular cells or spiral ganglion cells. Furthermore, there are several factors impacting one's faculty of hearing, for example, a great deal of noise in the environment and heredity. This kind of hearing loss is called sensorineural hearing loss, which cannot be cured surgically or medically in most cases. Nowadays, hearing-impaired patients usually wear audio devices such as hearing aids capable of amplifying sounds to enhance their hearing.

Before a hearing-impaired patient buys a hearing aid from a hearing-aid company, the professional performs a series of fitting and fine-tuning procedures depending on the disorder degree to allow the hearing-impaired patient to have a suitable hearing aid. The fitting and fine-tuning procedures include the following steps.

The first step is pre-fitting evaluation and audiometry (or so-called hearing test). At first, the audiologist or dispenser/hearing aid specialist gives a hearing test after the customer gets in the hearing-aid company.

The second step is hearing-aid fitting. The audiologist selects a suitable hearing aid for the customer within the budget limit according to the audiometric report. Then, the audiologist operates a fitting software provided by the manufacturer of the hearing aid to set parameters of the hearing aid. The audiologist may utilize several programs for the hearing aid to meet the customer's hearing requirements in different listening situations.

The third step is hearing-aid fine-tuning The customer expresses his/her feeling about the sounds and trouble encountered. The audiologist empirically fine-tunes parameters of the hearing aid to meet the customer's requirements and preferences.

The fourth step is trial use. The customer may take the hearing aid on trial for several weeks. If the hearing aid is not satisfying, the customer has to make an appointment with the audiologist to fine-tune the hearing aid again. The third step and the fourth step are repeated till the customer is satisfied with the hearing aid.

Figure 1:
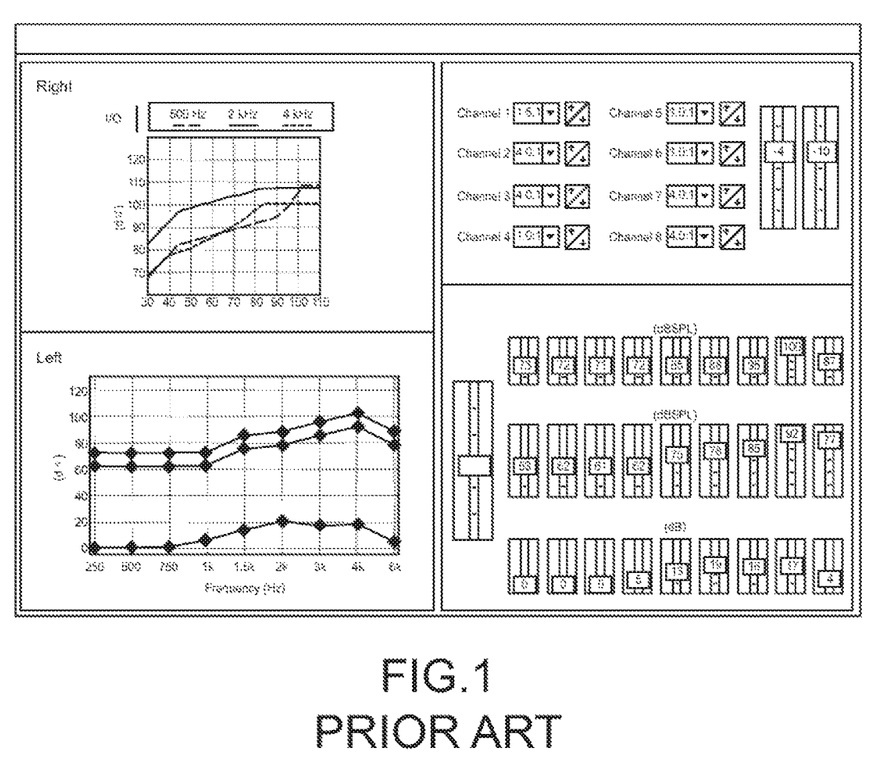
FIG. 1 illustrates a conventional user interface provided by a hearing aid fitting software used by a hearing-aid company for fine-tuning the hearing aid.

However, according to the above steps, it is known that the hearing aid fine-tuning step needs audiologist's experience cooperating with fitting software provided by the manufacturer of the hearing aid to fine-tune the hearing aid. That is to say, the customer has to carry the hearing aid back to the hearing-aid company again and again to perform the fine-tuning step if the adjustment is not satisfying. It is really costly and time-consuming. Someone may even return the hearing aid back or leave the hearing aid unused. In addition, the fitting software used for fine-tuning the hearing aid has a user interface incomprehensible to and difficult to be operated by unskilled persons. Please refer to FIG. 1 illustrating a user interface provided by a hearing aid fitting software usually used by a hearing aid company for fine-tuning the hearing aid. It is obvious that the user interface involves many complex parameters. For example, even the basic volume adjustment involves many frequency parameters and gain parameters to be adjusted to meet the user's requirement. Unfortunately, normal users have no idea how to perform the adjustment. If the customer installs the fitting software in his/her own computer equipped with a hearing-aid programmer to fine-tune the hearing aid by himself/herself, it is not easy for the customer to successfully adjust the hearing aid to satisfy his/her needs and preferences. Moreover, the hearing-aid programmer is not available for normal users. Hence, it is desired to overcome the above-mentioned problems.

SUMMARY OF THE INVENTION

The present invention provides a method for adjusting parameters of an audio device applied to an adjusting system operated by a user to adjust the audio device. The method includes steps of: executing an application program with the adjusting system; the application program providing a graphical user interface for receiving data wherein the graphical user interface at least comprises a plurality of options to be selected; and adjusting a plurality of parameters of the audio device associated with a first option when the first option of the plurality options is selected and outputting a sound by the audio device.

In an embodiment, the application program reduces the number of the plurality of options of the graphical user interface from a first number to a second number according to an audiometric result.

In an embodiment, the audiometric result is acquired from an audiometry for the user.

In an embodiment, the audiometry is controlled by the application program and performed by means of the audio device. The audiometry includes an air-conduction threshold test, an air-conduction most comfortable level test, or an air-conduction un-comfortable level test.

In an embodiment, the adjusting system, which executes the application program, controls a sound-receiving unit of the audio device to detect a surrounding noise. The adjusting system receives a detection result from the sound-receiving unit and compares the volume of the surrounding noise with a threshold value. If the volume of the detected surrounding noise exceeds the threshold value, it means that the surrounding noise may affect the reliability of the audiometric result. Then, the adjusting system shows through a screen a warning message to indicate that the current condition is improper for the audiometry, and shows a prompt message to teach how to diminish the influence of the surrounding noise.

In an embodiment, the sound-receiving unit of the audio device can detect a test sound to be judged by the user after the step of adjusting the plurality of the parameters associated with the selected first option.

In an embodiment, the test sound is a voice, the surrounding noise or a combination of both, and the test sound is produced by a speaker of the adjusting system or the audio device.

In an embodiment, the method for adjusting parameters of an audio device includes steps of: selecting a second option from the plurality of options after the sound is outputted by the audio device after the step of adjusting the plurality of parameters associated with the first option; and adjusting a plurality of parameters of the audio device associated with the second option and outputting a sound by the audio device.

In an embodiment, the first option includes a first comparative option and a second comparative option. A plurality of parameters of the audio device associated with the first comparative option or the second comparative option are adjusted in response to the selection of the first comparative option or the second comparative option to output the sound by the audio device.

In an embodiment, the adjusting system is a personal computer, a notebook computer, a mobile phone or a portable electronic device connected to a remote controller or an adjuster capable of adjusting the parameters of the audio device in a wired or wireless manner. The graphical user interface provided by the application program is shown on a screen of the personal computer, the notebook computer, the mobile phone or the portable electronic system.

In an embodiment, the adjusting system is an embedded device capable of adjusting the parameters of the audio device. The graphical user interface provided by the application program is shown on a display of the embedded device.

In an embodiment, the audio device is a hearing aid, a Bluetooth earphone, an amplified phone or a multimedia device.

The present invention provides another method for adjusting parameters of an audio device applied to an adjusting system operated by a user to adjust the audio device. The method includes steps of: executing an application program with the adjusting system; the application program providing a question-and-answer option graphical user interface for receiving data wherein the question-and-answer option graphical user interface at least includes a plurality of question items to be answered; and performing a first adjustment for the audio device according to a first answer to a first question item of the plurality of question items and outputting a sound by the audio device.

In an embodiment, the method for adjusting parameters of the audio device includes a step of: performing a second adjustment for the audio device according to a second answer to the first question item of the plurality of question items and outputting another sound by the audio device.

In an embodiment, the second adjustment for the audio device keeps the parameters of the audio device unchanged.

In an embodiment, the application program reduces the number of the plurality of question items of the question-and-answer option graphical user interface from a first number to a second number according to an audiometric result.

In an embodiment, the audiometric result is acquired from an audiometry for the user.

In an embodiment, the audiometry is controlled by the application program and performed by means of the audio device. The audiometry includes an air-conduction threshold test, an air-conduction most comfortable level test, or an air-conduction un-comfortable level test.

In an embodiment, the adjusting system is a personal computer, a notebook computer, a mobile phone or a portable electronic device connected to a remote controller or an adjuster capable of adjusting the parameters of the audio device in a wired or wireless manner. The graphical user interface provided by the application program is shown on a screen of the personal computer, the notebook computer, the mobile phone or the portable electronic device.

In an embodiment, the adjusting system is an embedded device capable of adjusting the parameters of the audio device. The graphical user interface provided by the application program is shown on a display of the embedded device.

In an embodiment, the audio device is a hearing aid, a Bluetooth earphone, an amplified phone or a multimedia device.

BRIEF DESCRIPTION OF THE DRAWINGS

The above objects and advantages of the present invention will become more readily apparent to those ordinarily skilled in the art after reviewing the following detailed description and the accompanying drawings, in which.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 2A:
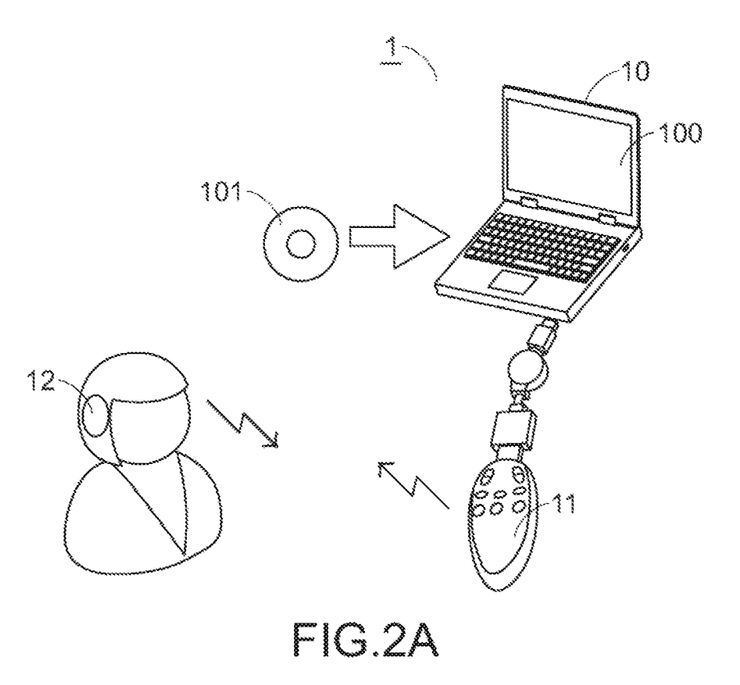
FIGS. 2A~C are schematic diagrams illustrating a first preferred embodiment of interfaces based on a method for adjusting parameters of an audio device according to the present invention.
Figure 2B:
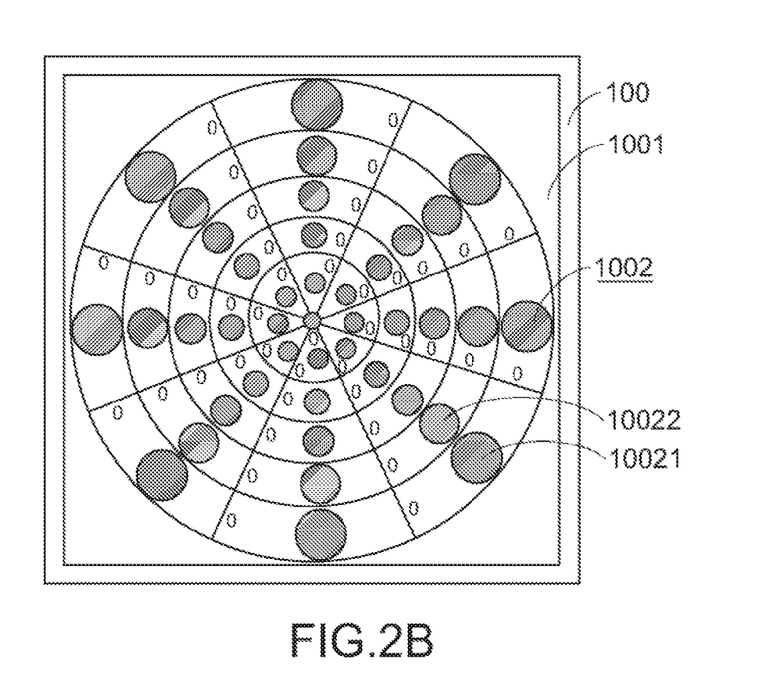
Figure 2C:
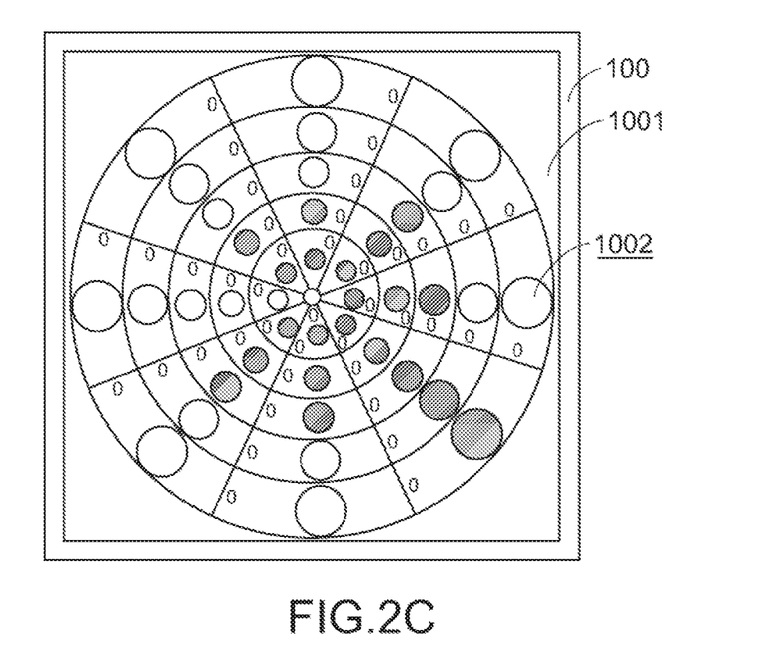

Please refer to FIGS. 2A~C, which are schematic diagrams illustrating a first preferred embodiment of a method for adjusting parameters of an audio device according to the present invention. In this preferred embodiment, a hearing aid adjusting system 1 includes a computer system 10 connected to a hearing aid remote controller 11 with adjusting function (or conventional hearing aid programmer), as shown in FIG. 2A. The method for adjusting parameters of the audio device according to the present invention is applied to the hearing aid adjusting system 1 to adjust a hearing aid 12. It is clear from the drawing that the computer system 10 executes a fitting software 101 associated with the hearing aid. When the user operates the hearing aid fitting software 101 through the computer system 10, a graphical user interface, to be operated by the user, is shown on a screen 100 of the computer system 10, as shown in FIG. 2B.

In this embodiment, the graphical user interface is, for example, a user interface 1001 with open-ended options provided by the fitting software 101. When the user is going to fine-tune the hearing aid 12, the user may select from the plurality of options 1002 provided by the open-ended option user interface 1001 to perform the fine-tuning step for the hearing aid 12. If the user select a first option 10021 from the options 1002 provided by the open-end option graphical user interface 1001, a plurality of parameters of the hearing aid 12 associated with the selected first option 10021 are adjusted.

After the adjustment of the hearing aid 12, the adjusted sound is outputted from a speaker (not shown) of the hearing aid 12. The user determines whether the adjusted sound is acceptable and suitable.

As mentioned above, if the adjusted sound obtained by adjusting parameters of the hearing aid 12 according to the first option 10021 is considered unsatisfying, the user may select a second option 10022 from the plurality of options 1002 provided by the open-ended graphical option user interface 1001. In a similar way, a plurality of parameters of the hearing aid 12 associated with the selected second option 10022 are adjusted. The parameters associated with the second option 10022 are not identical to those associated with the first option 10021. Of course, the parameters associated with the second option 10022 may partially overlap with those associated with the first option 10021. After the second option 10022 is selected and the plurality of parameters of the hearing aid 12 associated with the second option 1022 are adjusted, this adjusted sound is different from the adjusted sound corresponding to the first option 10021. Hence, the user may select different options to set different parameters and compares the sound outputted from the hearing aid 12, thereby finding the favorite sound property. Hence, through the easy-to-understand graphical user interface, the user of the hearing aid can operate the use interface easily. When the user needs to fine-tune the hearing aid after the purchase, the user can fine-tune the hearing aid as needed without another appointment with the audiologist to have the hearing aid fine-tuned. The method for adjusting parameters of the hearing aid according to the present invention is described in more detail in the following paragraphs.

As described above, form FIG. 2B, it is observed that the plurality of options 1002 in the open-ended graphical user interface 1001 are selectable. In fact, during the hearing aid fitting step, an audiometry including an air-conduction threshold test, an air-conduction most comfortable level test, or an air-conduction un-comfortable level test is given to the user. An audiometric result is obtained after these audiometries. The audiometric result obtained from the audiometries is inputted to the computer system 10 by the user, and the hearing aid fitting software 101 executed by the computer system 10 may decrease the available options 1002 to open less options in the open-ended option graphical user interface 1001. For example, as shown in FIG. 2C, after the audiometric result obtained from the audiometry is inputted, the available options 1002 are adjusted from the original forty options to twenty-one options. The twenty-one options are considered as proper options suitable for the user according to the audiometric result. Since the selectable options 1002 decreases, the user can select the options 1002 in the open-ended option graphical user interface to fine-tune the hearing aid more effectively. Furthermore, the audiometries are controlled by the hearing aid fitting software 101 executed by the computer 10 to perform the audiometries by means of the hearing aid 12 which produces a test sound such as a pure tone, a narrow-band noise and a warble tone. Sometimes, the test sound may be outputted through a speaker (not shown) of the computer system 10.

In addition, before the audiometry, a sound-receiving unit, e.g. a microphone (not shown) of the hearing aid 12 may detect the sound volume in the environment and transmit the detection to the hearing aid adjusting system 1. The hearing aid adjusting system 1 with the hearing aid fitting software 101 determines whether the surrounding noise volume exceeds a threshold value. If the surrounding noise volume exceeds the threshold value, it is possibly that the surrounding noise will affect the reliability of the audiometric result. Hence, the hearing aid adjusting system 1 shows a warning message through the screen 100 of the computer system 10 to indicate that the current condition is improper for the audiometry, and shows a prompt message to teach how to diminish the influence of the surrounding noise. It can ensure that the audiometry is performed without interference with surrounding noise so as to acquire more precise audiometric result. Furthermore, the sound receiver of the hearing aid 12 may be used for detecting a test sound selected from the above-mentioned background noise, a voice and a combination of both. The test sound is then outputted through the speaker of the hearing aid 12 or the computer system 10 to allow the user to decide whether to accept the outputted test sound after the adjustment of the parameters.

From the above description, it is clear that the method for adjusting parameters of a hearing aid according to the present invention provides a simple graphical user interface. It is helpful because the user can easily adjust the purchased hearing aid without seeking help from the hearing aid company. The present invention overcomes the problems resulting from the unfriendly user interface of the prior arts. In this embodiment, the audiometric result is acquired by controlling the hearing aid 12 to perform the audiometry with the hearing aid fitting software 101 executed by the computer system 10. Alternatively, the audiometry may be performed in hearing-aid company or hospital to acquire the audiometric result to be inputted for the hearing aid fitting software 101 executed by the computer system 10.

Figure 3:
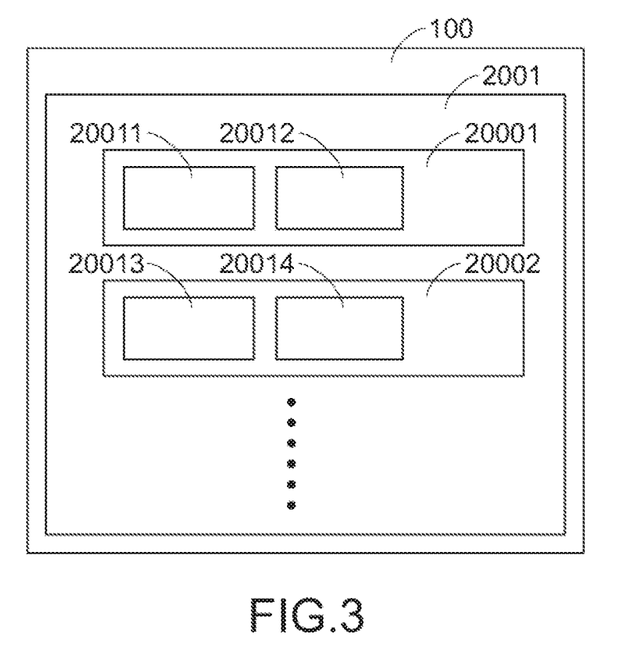
FIG. 3 is a schematic diagram illustrating a second preferred embodiment of an interface based on a method for adjusting parameters of an audio device according to the present invention.

Please refer to FIG. 3, a schematic diagram illustrating a second preferred embodiment of a method for adjusting parameters of an audio device according to the present invention. The adjusting method described in the embodiment is applied to the hardware environment of FIG. 2A. It is clearly shown that the graphical user interface provided by the present invention is a comparative option graphical user interface 2001. When the user is going to fine-tune the hearing aid 12, it can be done by selecting one option from the two comparative options provided by the comparative option graphical user interface 2001. For example, the comparative option first provides a first option menu 20001 including a first comparative option 20011 and a second comparative option 20012. The user selects a preferred one from the two options. After the selection from the first option menu 20001, a second option menu 20002 including a third comparative option 20013 and a fourth comparative option 20014 follows. When the user selects a preferred option, the first comparative option 20011 for example, from the first comparative menu 20001 for setting, it means that the first comparative option 20011 is better than the second comparative option 20012, but probably not the optimal setting. The user may proceed to select a preferred option from the second option menu 20002 provided by the comparative option graphical user interface 2001. Comparison and selection repeat till the optimal parameter setting of the hearing aid is obtained. Besides, part of technical means of the embodiment is similar to the first preferred embodiment and repetitious details are not given herein.

Figure 4:
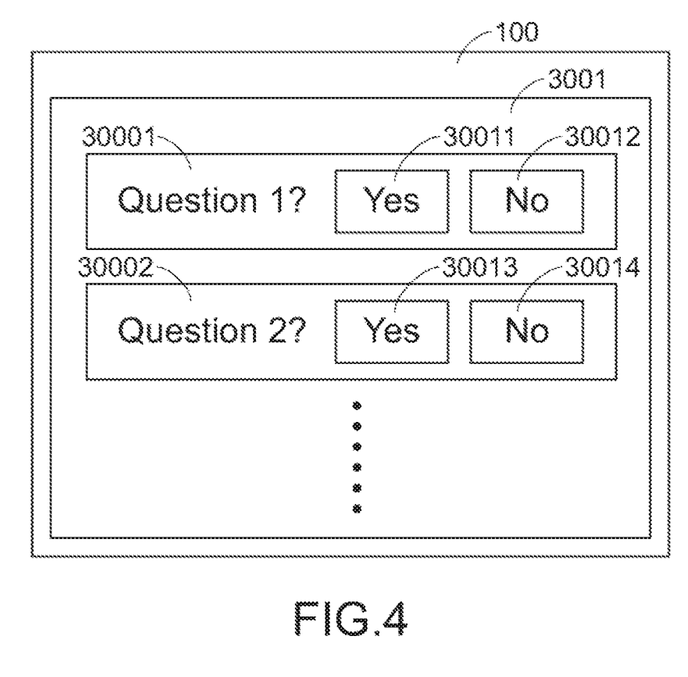
FIG. 4 is a schematic diagram illustrating a third preferred embodiment of an interface based on a method for adjusting parameters of an audio device according to the present invention.

Please refer to FIG. 4, a schematic diagram illustrating a third preferred embodiment of a method for adjusting parameters of an audio device according to the present invention. The adjusting method described in the embodiment is applied to the hardware environment of FIG. 2A. It is clearly shown that the graphical user interface provided by the present invention is a question-and-answer option graphical user interface 3001. When the user is going to fine-tune the hearing aid 12, it can be done by selecting one answer option according to the question provided by the question-and-answer option graphical user interface 3001. The question-and-answer option graphical user interface 3001 shows a first question item 30001 along with a "Yes" option 30011 and a "No" option 30012. The user may select one option from the "Yes" option 30011 and the "No" option 30012 according to the question associated with the first question item 30001. When the user finishes the selection for the first question item 30001, the question-and-answer option graphical user interface 3001 provides a second question item 30002 along with a "Yes" option 30013 and a "No" option 30014 to be selected. For example, the question in the first question item 30001 reads "Is the sound unclear?" If the user selects the "Yes" option 30011, the clarity setting of hearing aid is adjusted and then the second question item 30012 asks again "Is the sound unclear?" On the other hand, if the user selects the "No" option 30012 of the first question item 30001, the setting of the hearing aid keeps unchanged. Then, the method proceeds to the second question item 30012 associated with parameters other than clarity problem. Accordingly, the user can find out the optimal parameters through the question-and-answer mode. Besides, part of technical means of the embodiment is similar to the first preferred embodiment and repetitious details are not given herein.

Figure 5:
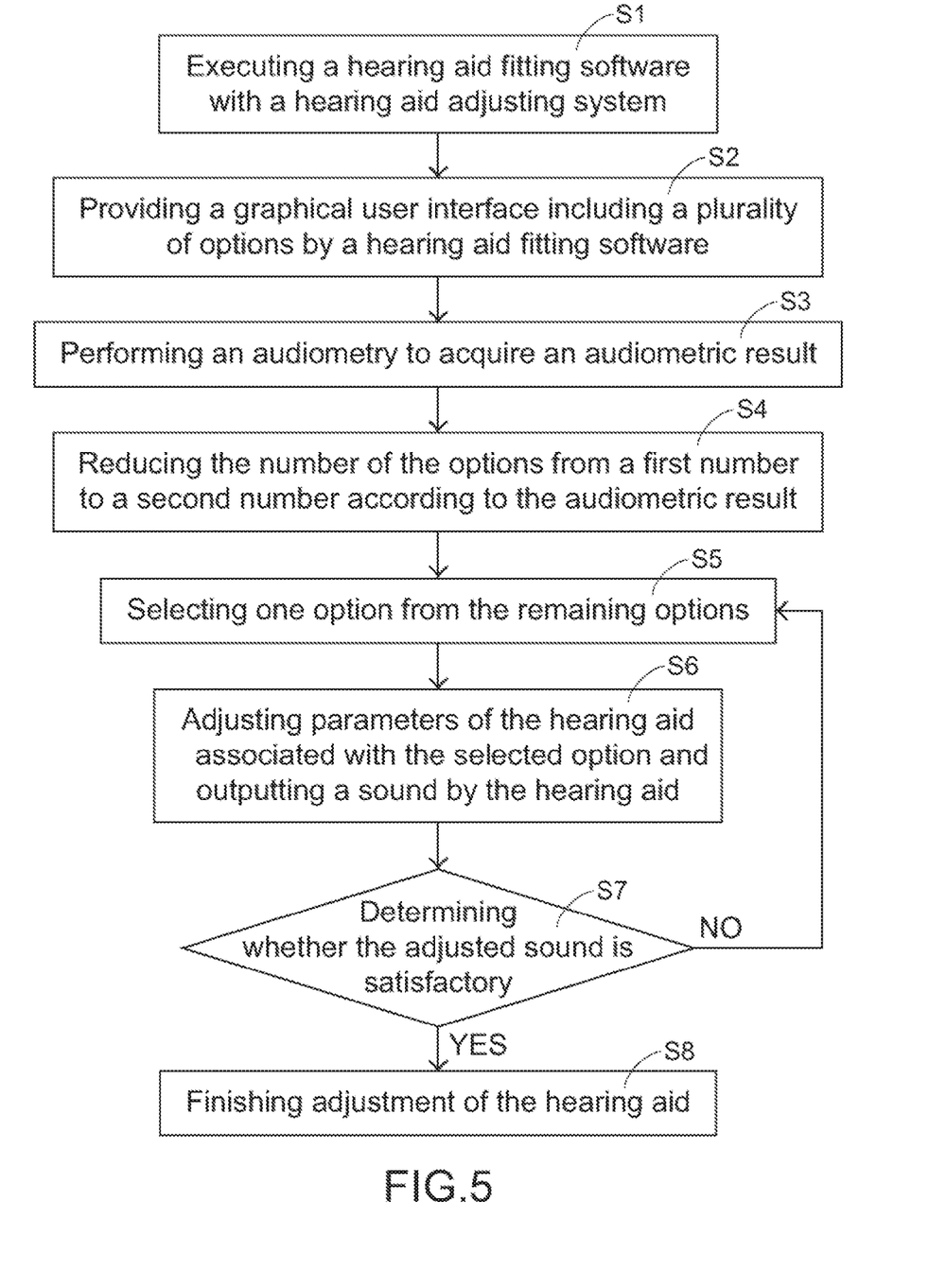
FIG. 5 is a flow chart illustrating the steps of a method for adjusting parameters of an audio device according to the present invention.

Please refer to FIG. 5, a flow chart illustrating the steps of a method for adjusting parameters of an audio device according to the present invention. The adjusting method described in the embodiment is applied to the hardware environment of FIG. 2A. It is clearly shown that a hearing aid fitting software is executed by the hearing aid adjusting system (step S1). The hearing aid fitting software provides a graphical user interface including a plurality of options (step S2). An audiometric result is acquired from an audiometry (step S3). The number of available options provided by the graphical user interface is reduced from a first number to a second number according to the audiometric result (step S4). One of the remaining options is selected (step S5). The parameters of the hearing aid associated with the selected option are adjusted and an adjusted sound is outputted by the hearing aid (step S6). The user determines whether the adjusted sound is satisfactory (step S7). If the sound from the adjusted hearing aid is satisfactory, the adjustment of the hearing aid finishes (step S8). If the sound from the adjusted hearing aid is unsatisfactory, the method goes to step S5 to select another one of the remaining options. Steps S5~S7 are repeated till the sound form the adjusted hearing aid is satisfactory.

Figure 6:
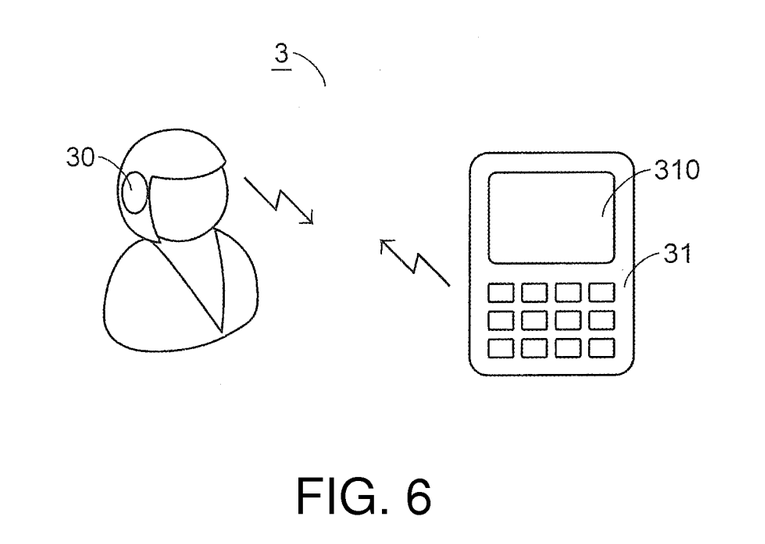
FIG. 6 is a schematic diagram illustrating another hardware environment to which a method for adjusting parameters of an audio device according to the present invention is applied.

In conclusion, the embodiments according to the present invention can improve the complicated and unfriendly user interface of the prior arts to achieve the purpose of the present invention. The given embodiments, however, are not limiting the appended claims of present invention. The technique of the present invention can be broadly applied to any audio device such as a Bluetooth earphone, an amplified phone or a multimedia device. Furthermore, the use of the adjusting system utilizing the method for adjusting parameters of an audio device according to the present invention is not limited to the hardware environment of FIG. 2A, but may be applied to a hardware environment including an adjusting system 3, as shown in FIG. 6. An embedded device 31 with the function of adjusting parameters of an audio device is used for adjusting the parameters of the hearing aid in a wireless manner (or in a wired manner). The fitting software (i.e. above-described application program) is built in the embedded device 31 and the graphical user interface is directly shown on a display 310 of the embedded system to be operated by the user.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for adjusting parameters of an hearing aid, applied to an adjusting system operated by a user to adjust the hearing aid, the method comprising steps of:
   executing an application program with the adjusting system;
   the application program providing a graphical user interface for receiving data, the graphical user interface comprising a first number of options to be selected; and
   adjusting a plurality of parameters of the hearing aid associated with a first option when the first option of the first number of options is selected and outputting a first sound by the hearing aid;
   reducing the number of the plurality of options of the graphical user interface from the first number to a second number according to an audiometric result aquired from an audiometric air-conduction threshold test, an air-conduction most comfortable level test, or an air-conduction uncomfortable level test, after the adjustment of the parameters of the hearing aid associated with the first option has been performed; and
   storing the adjusted parameters in the hearing aid.

2. The method according to claim 1, further comprising steps of:
   detecting a surrounding noise with a sound-receiving unit of the hearing aid controlled by the adjusting system with the application program;
   the adjusting system receiving a detection result from the sound receiver and comparing the volume of the surrounding noise with a threshold value; and
   showing a warning message and a prompt message on a screen of the adjusting system to indicate how to diminish the influence of the surrounding noise when the volume of the surrounding noise exceeds the threshold value.

3. The method according to claim 2 wherein the sound-receiving unit of the hearing aid detects a test sound to be judged by the user after the step of adjusting the plurality of the parameters associated with the selected first option.

4. The method according to claim 3 wherein the test sound is one selected from a voice, the surrounding noise and a combination, and the test sound is produced by a speaker of the adjusting system or the hearing aid.

5. The method according to claim 1, further comprising steps of:
   selecting a second option from the plurality of options after the first sound is outputted by the hearing aid after the step of adjusting the plurality of parameters associated with the first option; and
   adjusting a plurality of parameters of the audio device associated with the second option and outputting a second sound by the hearing aid.

6. The method according to claim 1 wherein the first option comprises a first comparative option and a second comparative option, and a plurality of parameters of the hearing aid associated with the first comparative option or the second comparative option are adjusted in response to the selection of the first comparative option or the second comparative option to output the first sound by the hearing aid.

7. The method according to claim 6 wherein the adjusting system is a personal computer, a notebook computer, a mobile phone or a portable electronic device connected to a remote controller or an adjuster capable of adjusting the parameters of the hearing aid in a wired or wireless manner, and the graphical user interface provided by the application program is shown on a screen of the personal computer, the notebook computer, the mobile phone or the portable electronic device.

8. The method according to claim 1 wherein the adjusting system is an embedded device capable of adjusting the parameters of the hearing aid, and the graphical user interface provided by the application program is shown on a display of the embedded device.

9. The method according to claim 1 wherein the hearing aid is additionally a Bluetooth earphone, an amplified phone or a multimedia device.

10. A method for adjusting parameters of an hearing aid, applied to an adjusting system operated by a user to adjust the hearing aid, the method comprising steps of:

executing an application program with the adjusting system;

the application program providing a question-and-answer option graphical user interface for receiving data, the question-and-answer option graphical user interface comprising a first number of question items to be answered;

performing a first adjustment for the hearing aid according to a first answer to a first question item of the first number of question items and outputting a sound by the hearing aid;

reducing the number of the plurality of question items of the question-and-answer option graphical user interface from the first number to a second number according to an audiometeric result aquired from an audiometeric air-conduction threshold test, an air-conduction most comfortable level test, or an air-conduction un-comfortable level test, after the first adjustment has been performed; and storing the adjusted parameters in the hearing aid.

11. The method according to claim 10, further comprising a step of:

performing a second adjustment for the hearing aid according to a second answer to the first question item of the plurality of question items and outputting another sound by the hearing aid.

12. The method according to claim 11 wherein the second adjustment for the hearing aid keeps the parameters of the hearing aid unchanged.

13. The method according to claim 10 wherein the adjusting system is a personal computer, a notebook computer, a mobile phone or a portable electronic device connected to a remote controller or an adjuster capable of adjusting the parameters of the hearing aid in a wired or wireless manner, and the graphical user interface provided by the application program is shown on a screen of the personal computer, the notebook computer, the mobile phone or the portable electronic device.

14. The method according to claim 10 wherein the adjusting system is an embedded device capable of adjusting the parameters of the hearing aid, and the graphical user interface provided by the application program is shown on a display of the embedded device.

15. The method according to claim 10, wherein the hearing aid is additionally a Bluetooth earphone, an amplified phone, or a multimedia device.

\* \* \* \* \*